(12) United States Patent
Pathi et al.

(10) Patent No.: US 8,258,294 B2
(45) Date of Patent: Sep. 4, 2012

(54) PROCESS FOR THE PREPARATION OF TEMOZOLOMIDE AND ANALOGS

(75) Inventors: Srinivas Laxminarayan Pathi, Karnataka (IN); Dharmaraj Ramachandra Rao, Mumbai (IN); Rajendra Narayanrao Kankan, Mumbai (IN)

(73) Assignee: CIPLA Limited, Mumbai (IN)

( * ) Notice: Subject to any disclaimer, the term of this patent is extended or adjusted under 35 U.S.C. 154(b) by 534 days.

(21) Appl. No.: 12/442,516

(22) PCT Filed: Sep. 28, 2007

(86) PCT No.: PCT/GB2007/003726
§ 371 (c)(1), (2), (4) Date: Jun. 16, 2009

(87) PCT Pub. No.: WO2008/038031
PCT Pub. Date: Apr. 3, 2008

(65) Prior Publication Data
US 2009/0326028 A1 Dec. 31, 2009

(30) Foreign Application Priority Data
Sep. 29, 2006 (IN) .......................... 1611/MUM/2006

(51) Int. Cl.
C07D 487/04 (2006.01)
C07D 233/90 (2006.01)
A61K 31/4188 (2006.01)
A61P 35/00 (2006.01)

(52) U.S. Cl. .................................... 544/179; 548/326.5
(58) Field of Classification Search .................. 544/179; 548/326.5
See application file for complete search history.

(56) References Cited

U.S. PATENT DOCUMENTS

| 5,260,291 | A | 11/1993 | Lunt et al. | |
| 7,087,751 | B2 * | 8/2006 | Kuo et al. | 544/179 |
| 7,334,688 | B2 | 2/2008 | Pahl et al. | |
| 7,446,209 | B2 * | 11/2008 | Kuo et al. | 548/326.5 |
| 7,612,202 | B2 * | 11/2009 | Etlin et al. | 544/179 |
| 7,737,284 | B2 * | 6/2010 | Kuo et al. | 548/326.5 |
| 2002/0013306 | A1 | 1/2002 | Lowe | |
| 2002/0095036 | A1 * | 7/2002 | Kuo et al. | 544/179 |
| 2005/0131227 | A1 | 6/2005 | Kuo et al. | |
| 2006/0183898 | A1 * | 8/2006 | Etlin et al. | 544/179 |

FOREIGN PATENT DOCUMENTS
WO 2008038031 A1 4/2008

OTHER PUBLICATIONS

Horton, Julie K., "Triazines and related products. Part 23. New photoproducts from 5-diazoimidazole-4-carboxamide (diazo-IC)," J. Chem. Soc., Perkin Transaction I, 1981, pp. 1433-1436, The Royal Society of Chemistry.

Shealy, Y. Fulmar, et al., "Synthesis of potential anticancer agents. XXIX. 5-diazoimidazole-4-carboxamide and 5-diazo-v-triazole-4-carboxamide," J. Org. Chem., 1961, pp. 2396-2401, vol. 26, American Chemical Society.

Wheelhouse, Richard T., "Antitumour imidazotetrazines. Part 31. The synthesis of isotopically labelled temozolomide and a multinuclear (1H, 13C, 15N) magnetic resonance investigation of temozolomide and mitozolomide," J. Chem. Soc., Perkin Transaction I, 1995, pp. 249-252, No. 3, The Royal Society of Chemistry.

Foreign communication from a corresponding application—Third party observations, European patent application No. 7823983, May 28, 2010, 17 pages.

Foreign communication from a priority application—International Preliminary Report on Patentability, PCT/GB2007/003726, Feb. 25, 2009, 13 pages.

Foreign communication from a priority application—International Search Report and Written Opinion, PCT/GB2007/003726, Dec. 20, 2007, 13 pages.

Stevens, Malcolm F. G., et al., "Antitumor imidazotetrazines. 1. Synthesis and chemistry of 8-carbamoyl-3-(2-chloroethyl)imidazo[5,1-d]-1,2,3,5-tetrazin-4(3H)-one, a novel broad-spectrum antitumor agent," Journal of Medicinal Chemistry, 1984, pp. 196-201, vol. 27, No. 2, American Chemical Society.

Wang, Yongfeng, et al., "Alternative syntheses of the antitumour drug temozolomide avoiding the use of methyl isocyanate," Chem. Commun., J. Chem. Soc., 1994, pp. 1687-1688.

Wang, Yongfeng, et al., "Antitumor imidazotetrazines. 35. New synthetic routes to the antitumor drug temozolomide," J. Org. Chem., 1997, pp. 7288-7294, vol. 62, No. 21, American Chemical Society.

* cited by examiner

*Primary Examiner* — Venkataraman Balasubramanian
(74) *Attorney, Agent, or Firm* — Conley Rose, P.C.; Rodney B. Carroll

(57) ABSTRACT

A process for the preparation of compounds of formula IA, where $R=CH_3$ (i.e. temozolomide):

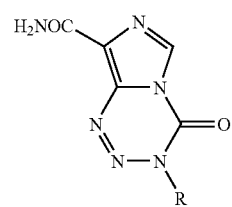

comprising diazotizing a compound of the formula IIA:

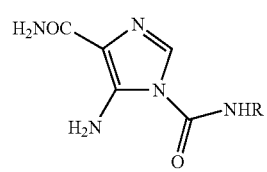

where in R is as defined above in the presence of at least one metal halide, an acid and a source of nitrous acid, followed by conversion of acidic solution containing temozolomide. The conversion can be carried out by a liquid-liquid extraction technique in a water immiscible solvent. The temozolomide may be further purified in an acetone-water mixture.

27 Claims, No Drawings

PROCESS FOR THE PREPARATION OF TEMOZOLOMIDE AND ANALOGS

CROSS-REFERENCE TO RELATED APPLICATIONS

This application is a filing under 35 U.S.C. 371 of International Application No. PCT/GB2007/003726 filed Sep. 28, 2007, entitled "An Improved Process for the Preparation of Temozolomide and Analogs," claiming priority of Indian Patent Application No. 1611/MUM/2006 filed Sep. 29, 2006, which applications are incorporated by reference herein in their entirety.

FIELD OF INVENTION

This invention relates to an improved process for the preparation of antitumour compound, temozolomide and analogs.

BACKGROUND OF THE INVENTION

Temozolomide, is a known antitumour drug, and is represented by formula I:

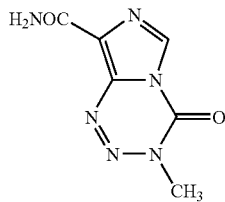

I 3-methyl-8-aminocarbonyl-imidazo[5,1-d]-1,2,3,5-tetrazin-4(3H)-one

It is described in U.S. Pat. No. 5,260,291 together with compounds of broadly similar activity such as higher alkyl analogs at the 3-position.

J. Med. Chem. 1984, 27, 196-201 describes a process wherein 5-amino-1H-imidazole-4-carboxamide is converted into 5-diazo-1H-imidazole-4-carboxamide, which is then cyclised with methylisocyanate in dichloromethane to provide a high yield of temozolomide.

This process requires isolation of the unstable and potentially dangerous 5-diazo-1H-imidazole-4-carboxamide, methyl isocyanate is a difficult reagent to handle and ship, especially on the industrial scale. Furthermore, the cycloaddition of methylisocyanate requires a long reaction time (Table I in J. Med. Chem. 1984, 27, 196-201, suggests 20 days).

The product obtained by this process contains high residual dichloromethane. It is essential to limit dichloromethane content in the final API below 600 ppm as per ICH guideline. Dichloromethane content can be reduced if one follows technique of U.S. Pat. No. 5,260,291.

U.S. Pat. No. 5,260,291 discloses acetone-water recrystalisation of temozolomide, which results in low yield (60% recovery) due to decomposition of temozolomide to impurities like 5-(3-methyltriazen-1-yl)imidazole-4-carboxamide, compound of formula V

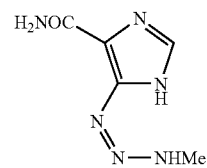

V and 5-amino-1H-imidazole-4-carboxamide.

The production of compound of formula I by the two processes described in J. Chem. Soc., Chem. Commun., 1994, 1687-1688 provides a low overall yield from 5-amino-1H-imidazole-4-carboxamide: less than 20% (about 17% through 5-diazo-1H-imidazole-4-carboxamide and about 15% through 5-amino-$N^1$-(ethoxy carbonylmethyl)-1H-imidazole-1,4-dicarboxamide).

The unstable 5-diazo-1H-imidazole-4-carboxamide has to be isolated in the branch of this process that uses it as an intermediate.

US 2002/0133006 discloses a process for the preparation of compound of formula I using methyl hydrazine which is a toxic and flammable liquid, hence not feasible on industrial scale and the final isolation involves tedious workup including column chromatography.

J. Org. Chem. 1997, 62, 7288-7294 describes a process wherein the final step of diazotization provides equi-formation of aza-hypoxanthine and temozolomide, resulting in low yield. This literature does not provide the experimental procedure for work up.

US 2005/0131227 describes a process involving the use of a bulky protecting group on nitrogen of the primary amide for cyclisation in presence of LiCl to minimize the undesired cyclization product. After cyclization the protecting group has to be removed which makes the process more laborious with more number of steps (Scheme I).

Scheme I:

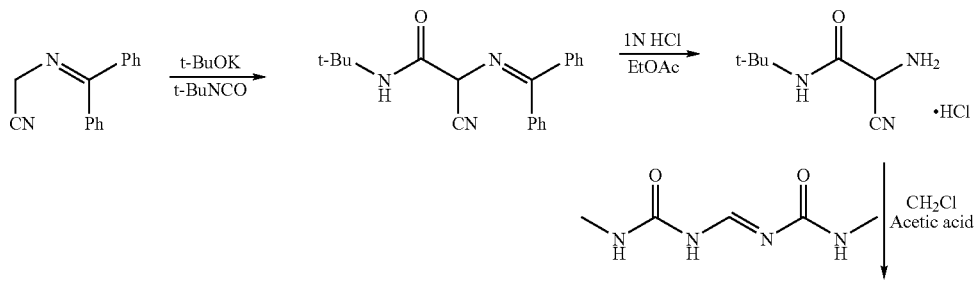

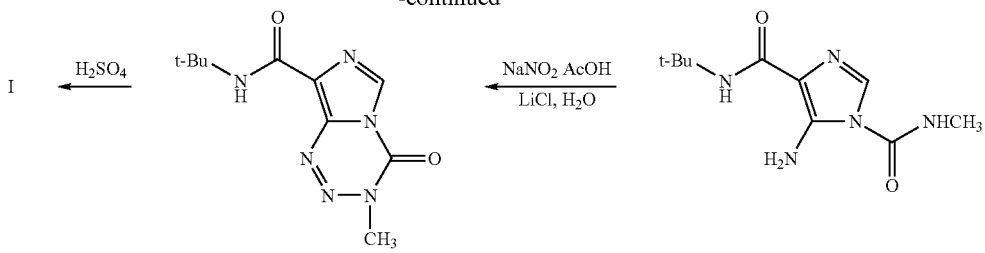

Because of the difficulties in the prior art, there is a need to develop a process for preparing temozolomide that is more convenient, especially on an industrial scale, to provide temozolomide in good yield and purity.

SUMMARY OF THE INVENTION

The present invention provides a process for the preparation of compounds of formula IA, where R=CH₃ (i.e. temozolomide):

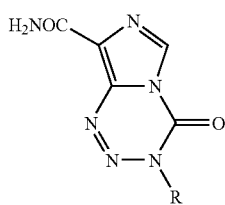

However, the process is also applicable to substitutions in which R is an alkyl group having from 1 to 6 carbon atoms,
According to the invention, the process comprises:
(a) diazotizing a compound of the formula IIA:

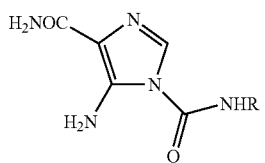

where in R is as defined above in the presence of metal halides to minimize undesired cyclisation product;

(b) optimizing the addition of reagents, where in acid solution of compound of formula IIA is added to the sodium nitrite solution to achieve better purity and yield;
(c) extracting the product of formula I by counter-current extraction using continuous liquid-liquid extraction technique.

DETAILED DESCRIPTION OF THE INVENTION

It is noted that cyclisation of the compound of formula IIA, proceeds in either direction resulting in equi-formation of desired compound of formula I (in particular, temozolomide) and an undesired compound of formula IV (aza-hypoxanthine).

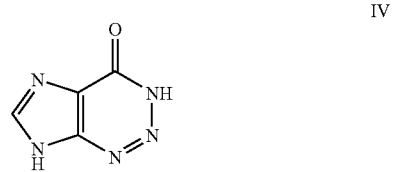

According to one embodiment of the present invention, diazotization reaction is carried out in presence of metal halides which promotes the cyclisation in desired direction to compounds of formula IA in high proportion, as shown in Scheme II below.

The metal halides is preferably a monovalent or divalent metal, such as an alkali metal, and alkaline earth metal or a suitable transition element metal. Particularly suitable metals include Li, Na, Zn, Mg, Ni, Ca, Cs. The preferred metal is Li. The halide may be an anions such as F, Cl, Br, I. The preferred halides are Cl and Br. The most preferred metal halides are LiCl and/or LiBr.

The compound of formula II can be prepared as described in *J. Org. Chem.* 1997, 62, 7288-7294.

Scheme II:

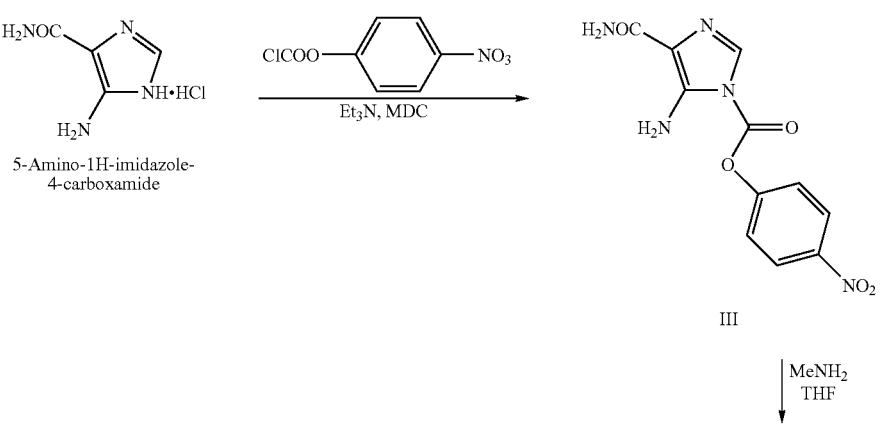

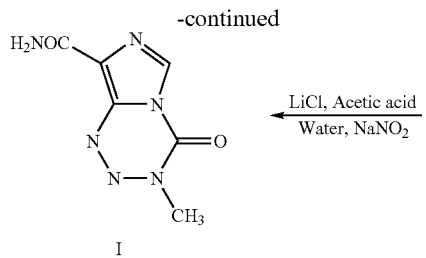 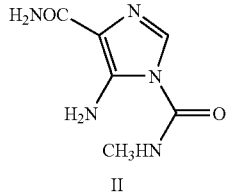

The conversion of compound of formula II to I requires consecutive diazotization and cyclisation. This reaction is preferably carried out in an aqueous and/or organic solution, preferably with a source of nitrous acid, most preferably in solution in an aqueous organic acid such as a lower alkanoic acid, such as acetic acid, tartaric acid, oxalic acid, etc. or an inorganic acid such as HCl, $H_2SO_4$, etc. The reaction can be conducted in water and/or water-miscible solvents such as lower alkanols (i.e. $C_{1-6}$ alkanols, especially $C_{1-4}$ alkanols), Tetrahydrofuran (THF), Dimethyl sulfoxide (DMSO), acetone and Dimethylformamide (DMF) etc. The reaction can also be effected in an organic solvent with an organic source of nitrous acid, e.g., t-butyl or isopentyl nitrite with a carboxylic acid such as a lower alkanoic acid, e.g. i.e., a $C_{1-6}$ alkanoic acid, such as acetic acid, and in an organic solvent such as lower alkanol (i.e. $C_{1-6}$ alkanols, especially $C_{1-4}$ alkanols), DMF, DMSO, acetone, THF, ethyl acetate, dichloromethane, chloroform or a hydrocarbon such as toluene, hexane or heptane. This process yields an acidic solution of temozolomide, which may be further purified to yield tomozolomide.

The reaction proceeds through a diazonium salt, which spontaneously cyclizes to the compound of formula I.

In all the processes described in the literature of temozolomide for diazotization reaction, nitrite solution is added to the acid solution of compound to be diazotized. With this method, the yield obtained is inconsistent and varies between 28 to 43%.

According to process of the present invention diazotization reaction is optimized by reverse addition wherein the amide of compound of formula II is added to the sodium nitrite solution to obtain consistently an yield of 43 to 65% (based on the method of extraction).

Temozolomide, as a free base, is insoluble in water. It is believed that in the conversion of a compound of formula II to temozolomide, temozolomide forms as a salt with acid and is soluble in water. Temozolomide is highly unstable at pH>5 (it decomposes to 5-(3-methyltriazen-1-yl)imidazole-4-carboxamide, the compound of formula V) and stable at pH<5.

V

Because of this instability of temozolomide in basic conditions, the conversion of temozolomide salt to temozolomide base in the usual conditions (treatment with base) is not feasible. The material can be isolated by conventional extraction, where in it requires huge volumes of solvent which is not viable industrially and cannot be extracted effectively.

According to yet another embodiment of the present invention, the isolation of temozolomide from its salt is carried out by counter-current extraction using a continuous liquid-liquid extraction technique using water immiscible solvent. Depending on the solvent, two types of apparatus can be used, liquid-liquid extraction either by upward displacement (for solvents lighter than water) or by downward displacement (for solvents heavier than water). During this process, the temozolomide salt dissociates into free base and the free base is extracted continuously by the solvent. It will be appreciated that the water immiscible solvent is a solvent which is capable of extracting the temozolomide base.

The water-immiscible solvent may be selected from group consisting of toluene, hexane, heptane, diethyl ether, diisopropyl ether, chlorinated solvents, and mixtures thereof. The preferred solvents are dichloromethane and hexane. It will be appreciated that other water-immiscible solvents may be used instead, the selection of which is within the normal skill of a person skilled in the art. According to this embodiment of the present invention, the efficiency of the extraction of temozolomide by using continuous liquid-liquid extraction technique is 90% as against 60% by conventional extraction technique.

According to yet another embodiment of the present invention, the desired desolvated temozolomide with good and efficient yield is obtained by desolvation technique which cannot be obtained by conventional technique of drying. The process involves stirring temozolomide in an acetone-water mixture having a pH of 3.0-4.0 at reflux temperature followed by recovery of the purified temozolomide, for example by cooling, filtration and drying.

The reflux temperature is preferably 52 to 55° C. The acetone-water ratio is preferably from 2.5:1 to 3.5:1, most preferably 3:1. The pH of 3-4 can be achieved by acidification of the water, preferably before mixing with the acetone. The water may be acidified with, for example, acetic acid, to provide an acidified water solution at a pH of 2.5 to 4.5, preferably 3.0 to 4.0. The refluxing may carried out for 45 to 75 minutes, with a refluxing time of 60 minutes being typical.

EXAMPLES

The invention will not be described with reference to the following examples, which are intended to illustrate the invention.

Example 1

Preparation of 3-Methyl-8-aminocarbonyl-imidazo [5,1-d]-1,2,3,5-tetrazin-4(3H)-one (Temozolomide)

Glacial acetic acid (25 ml), water (250 ml) and LiCl (225 g) were charged and the contents were stirred for 30 minutes and cooled to room temperature. 5-Amino-1-(N-methylcarbamoyl)imidazole-4-carboxamide (II) (25 g) was added and stirred the contents for further 30 minutes. The reaction mixture was cooled to 0° C. and then added drop wise to NaNO$_2$ solution (12.5 g in 50 ml water) at −10 to 5° C. The reaction mass was stirred for 1 hr at 0-5° C. and then at room temperature for 5 hrs. To this reaction mixture, sodium thiosulphate solution (25 g in 250 ml of water) was added slowly and stirred for 20 minutes (solution A). This process yielded an acidic solution containing temozolomide.

Example 2

Preparation of 3-Methyl-8-aminocarbonyl-imidazo [5,1-d]-1,2,3,5-tetrazin-4(3H)-one (Temozolomide) and Extraction by Conventional Technique Solution A as prepared above in Example 1 is extracted using dichloromethane (5.0 L×5), concentrated to 100 ml stage and filtered to give temozolomide (11.5 g, 43% yield, 99.0% HPLC purity).

Example 3

Preparation of 3-Methyl-8-aminocarbonyl-imidazo [5,1-d]-1,2,3,5-tetrazin-4(3H)-one (Temozolomide) and Extraction by Continuous Liquid-Liquid Extraction Technique Solution A as prepared above in Example 1 is extracted using dichloromethane (1000 ml) by continuous liquid-liquid extractor, concentrated to 100 ml stage and filtered to give temozolomide (17.2 g, 65% yield, 99.3% HPLC purity).

Example 4

Preparation of 3-Methyl-8-aminocarbonyl-imidazo [5,1-d]-1,2,3,5-tetrazin-4(3H)-one (Temozolomide)

Glacial acetic acid (50 ml), water (500 ml) and LiCl (450 g) were charged and the contents were stirred for 30 minutes and cooled to room temperature. 5-Amino-1-(N-methylcarbamoyl)imidazole-4-carboxamide (II) (50 g) was added and stirred the contents for further 30 minutes. The reaction mixture was cooled to 0° C. and then added drop wise to NaNO$_2$ solution (25 g in 100 ml water) at −10 to 5° C. The reaction mass was stirred for 1 hr at 0-5° C. and then at room temperature for 5 hrs. To this reaction mixture, sodium thiosulphate solution (50 g in 500 ml of water) was added slowly and stirred for 20 minutes. This process yielded an acidic solution containing temozolomide. This acidic solution was extracted using hexane (2000 ml) by continuous liquid-liquid extractor, concentrated to 100 ml stage and filtered to give temozolomide (33.4 g, 63% yield, 99.2% HPLC purity).

Example 5

Preparation of 3-Methyl-8-aminocarbonyl-imidazo [5,1-d]-1,2,3,5-tetrazin-4(3H)-one (Temozolomide)

Glacial acetic acid (25 ml), water (250 ml), LiBr (450 g) were charged and the contents were stirred for 30 minutes and cooled to room temperature. 5-Amino-1-(N-methylcarbamoyl)imidazole-4-carboxamide (II) (25 g) was added and stirred the contents for additional 30 minutes. The reaction mixture was cooled to 0° C. and then added drop wise to NaNO$_2$ solution (12.5 g in 50 ml water) at −10 to 5° C. The reaction mass was stirred for 1 hr at 0-5° C. and then at room temperature for 5 hrs. To this reaction mixture, sodium thiosulphate solution (25 g in 250 ml of water) was added slowly and stirred for 20 minutes. This process yielded an acidic solution containing temozolomide. This acidic solution was extracted using dichloromethane (1000 ml) by continuous liquid-liquid extractor, concentrated to 100 ml stage and filtered to give temozolomide (16.9 g, 64% yield, 99.4% HPLC purity).

Example 6

Preparation of 3-Methyl-8-aminocarbonyl-imidazo [5,1-d]-1,2,3,5-tetrazin-4(3H)-one (Temozolomide)

Glacial acetic acid (50 ml), water (500 ml) and LiCl (450 g) were charged and the contents were stirred for 30 minutes and cooled to room temperature. 5-Amino-1-(N-methylcarbamoyl)imidazole-4-carboxamide (II) (50 g) was added and stirred the contents for further 30 minutes. The reaction mixture was cooled to 0° C. and then added drop wise to sodium nitrite solution (25 g in 100 ml water) at −10 to 5° C. The reaction mass was stirred for 1 hr at 0-5° C. and then at room temperature for 5 hrs. To this reaction mixture, sodium thiosulphate solution (50 g in 500 ml of water) was added slowly and stirred for 20 minutes. This process yielded an acidic solution containing temozolomide. This acidic solution was extracted using dichloromethane (2000 ml) by continuous liquid-liquid extractor, concentrated to 100 ml stage and filtered the temozolomide.

To the above filtered temozolomide, acetone (350 ml) was charged at room temperature, heated to reflux (52-55° C.) and maintained for 5 hours, distilled off 50% of acetone atmospherically at 52-55° C., charged acetone (175 ml) and distilled off 50% of acetone atmospherically at 52-55° C., this process was repeated twice and 25% of aqueous acetone (350 ml, pH of water is acidified to 3.0 using acetic acid) was charged at 52° C. Refluxed the contents for 1 hour at 52° C., slowly cooled to room temperature in 1 hour and maintained at room temperature for 2 hours. Chilled the contents to 10° C., maintained for 1 hour, filtered the solid, washed with acetone (35 ml) and dried at 45-50° C. under vacuum to yield temozolomide (33.2 g, 62% yield, 99.8% HPLC purity, dichloromethane content: 250 ppm).

It will be appreciated that the invention described above may be modified within the scope of the claims.

What is claimed is:

1. A process for the preparation of a compound of formula IA, where R=CH$_3$ (i.e. temozolomide):

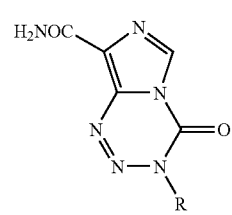

IA comprising:
(a) diazotizing a compound of the formula IIA:

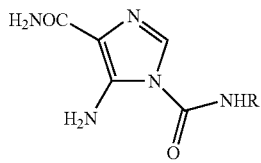

wherein R is as defined above in the presence of at least one lithium halide, an acid and a source of nitrous acid, wherein the diazotization proceeds by the addition of the compound of formula IIA and the metal halide to a solution containing the source of nitrous acid; and (b) extracting the temozolomide by subjecting the acidic solution of temozolomide prepared in step (a) to a counter-current continuous liquid-liquid extraction using a water-immiscible solvent.

2. The process according to claim 1, wherein the lithiun halide is LiCl and/or LiBr.

3. The process according to claim 1, wherein the source of nitrous acid is an inorganic source of nitrous acid.

4. The process according to claim 3, wherein the source of nitrous acid is $NaNO_2$.

5. The process according to claim 1, wherein the source of nitrous acid is an organic source of nitrous acid.

6. The process according to claim 5, wherein the source of nitrous acid is t-butyl nitrite or isopentyl nitrite.

7. A process for the preparation of compounds of formula IA, where R=$CH_3$ (i.e. temozolomide):

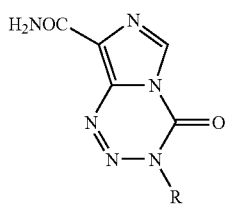

comprising:
(a) diazotizing a compound of the formula IIA in the presence of an acid:

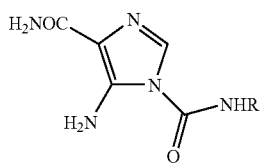

wherein R is as defined above by adding the compound of formula II to a nitrite source in the form of a solution; and (b) extracting the temozolomide by subjecting the acidic solution of temozolomide prepared in step (a) to a counter-current continuous liquid-liquid extraction using a water-immiscible solvent.

8. The process according to claim 7, wherein the solution includes an organic solvent.

9. The process according to claim 7, wherein the solution is an aqueous solution.

10. The process according to claim 7, wherein the nitrite source is $NaNO_2$.

11. The process according to claim 7, wherein the compound of formula II is added dropwise to the nitrite source.

12. The process according to claim 7, wherein the compound of formula II is mixed with a lithium halide before being added to the nitrite source.

13. The process according to claim 1, wherein the acid is an organic acid.

14. The process according to claim 13, wherein the organic acid is $C_{1-6}$ alkanoic acid, tartaric acid or oxalic acid.

15. The process according to claim 13, wherein the organic acid is acetic acid.

16. The process according to claim 1, wherein the acid is an inorganic acid.

17. The process according to claim 16, wherein the inorganic acid is HCl and $H_2SO_4$.

18. A process for isolating temozolomide from an acidic solution containing temozolomide comprising: subjecting the acidic solution of temozolomide to a counter-current continuous liquid-liquid extraction using water immiscible solvent.

19. The process according to claim 18, wherein the water-immiscible solvent is toluene, hexane, heptane, diethyl ether, diisopropyl ether, chlorinated solvents, or a mixture thereof.

20. The process according to claim 19, comprising recovering temozolomide from the water-immiscible solvent.

21. The process according to claim 18, further comprising purifying the temozolomide by refluxing temozolomide in an acetone-water mixture having a pH from 2.5 to 4.5 followed by recovering purified temozolomide.

22. The process according to claim 21, wherein the reflux temperature is 52 to 55° C.

23. The process according to claim 21, wherein the acetone-water ratio, on a volume basis, is 3:1.

24. The process according to claim 21, wherein the refluxing is carried out for 45 to 75 minutes.

25. The process according to claim 21, further comprising refluxing the temozolomide with acetone prior to refluxing with the acetone-water mixture.

26. The process according to claim 1, further comprising purifying the temozolomide by refluxing temozolomide in an acetone-water mixture having a pH from 2.5 to 4.5 followed by recovering purified temozolomide.

27. The process according to claim 7, further comprising purifying the temozolomide by refluxing temozolomide in an acetone-water mixture having a pH from 2.5 to 4.5 followed by recovering purified temozolomide.

* * * * *